United States Patent [19]

Cavender

[11] Patent Number: 4,565,875
[45] Date of Patent: Jan. 21, 1986

[54] IMIDAZOLE PLANT GROWTH REGULATORS

[75] Inventor: Patricia L. Cavender, Princeton Junction, N.J.

[73] Assignee: FMC Corporation, Philadelphia, Pa.

[21] Appl. No.: 625,056

[22] Filed: Jun. 27, 1984

[51] Int. Cl.[4] .......................................... C07D 233/90
[52] U.S. Cl. .................... 548/336; 546/278; 548/337; 548/342; 548/343
[58] Field of Search ................ 548/336, 337, 342, 343

[56] References Cited

U.S. PATENT DOCUMENTS

| | | | |
|---|---|---|---|
| 3,261,873 | 7/1966 | Johnson et al. | 260/309 |
| 3,501,286 | 3/1970 | Draber et al. | 71/92 |
| 3,915,982 | 10/1975 | Aida et al. | 260/309 |
| 4,139,365 | 2/1979 | Copping et al. | 71/92 |
| 4,220,466 | 9/1980 | Patel | 71/92 |

FOREIGN PATENT DOCUMENTS

| | | |
|---|---|---|
| 3044199 | 6/1982 | Fed. Rep. of Germany . |
| 140966 | 9/1980 | German Democratic Rep. . |
| 51-11765 | 1/1976 | Japan . |
| 57-167973 | 10/1982 | Japan . |
| 58-074670 | 5/1983 | Japan . |
| 654221 | 8/1965 | South Africa . |
| 2084140 | 4/1982 | United Kingdom . |

OTHER PUBLICATIONS

Balaban and Pyman, *J. Chem. Soc.*, 121, 947 (1922).
Buchman, et al., *J. Med. Chem.*, 17, 1168–73 (1974).
Chan, et al., *J. Org. Chem.*, 47, 3457 (1982).
Okamoto, et al., "Proceedings of Eighth International Conference on Plant Growth Substances," K. V. Thimann, Editor, Kirokawa, Tokyo, Japan 1974, pp. 447–455.
Sharnin, et al., *Chem. Hetero. Cmpds.*, 12, 1332 (1977).
Shaw, *J. Org. Chem.*, 30, 3371 (1965).
Matsubara, *Phytochemistry*, 19, 2239–53 (1980).
Novikov, et al., *Chem. Hetero. Cmpds.*, 6, 465 (1970).
Parkin and Harnden, *J. Heterocycl. Chem.*, 19, 33–40 (1982).
*Chem. Abstr.*, 97, 72365y (1982).
Fehr and Caviness, Special Report 80, Iowa State University, Ames, Iowa 50011, Mar. 1977.
Ferris and Orgel, *J. Am. Chem. Soc.*, 88, 3829–3831 (1966).
*Chem. Abstr.*, 90, 72190t (1979).
*Chem. Abstr.*, 91, 39482n (1979).
*Chem. Abstr.*, 93, 114521w (1980).
*Chem. Abstr.*, 81, 25900d (1974).
*Chem. Abstr.*, 83, 114409j (1975).
*Chem. Abstr.*, 90, 72189z (1979).

*Primary Examiner*—Paul R. Michl
*Attorney, Agent, or Firm*—R. L. Hansen; H. R. Ertelt

[57] ABSTRACT

Imidazoles of the following structural formula are plant growth regulators:

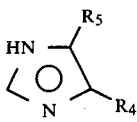

wherein
$R_4$ is selected from the group consisting of —H, —lower alkyl, —NO$_2$, —CN, and —CONHY; and
$R_5$ is selected from the group consisting of —NZCOR$_A$, —CONZR$_B$, —COOZ, —Cl, —Br, —CN, —NO$_2$,

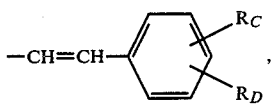

—NHZ,

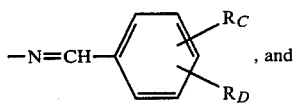

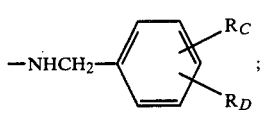

in which
Y is selected from the group consisting of —H, —lower alkyl, —aryl, and —substituted aryl;
Z is selected from the group consisting of —H and —lower alkyl;
$R_A$ is selected from the group consisting of —straight or branched alkyl, —lower alkoxyl,

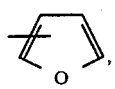

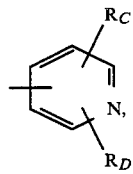

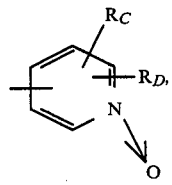

(Abstract continued on next page)

-continued
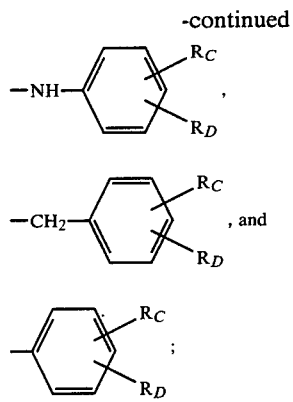
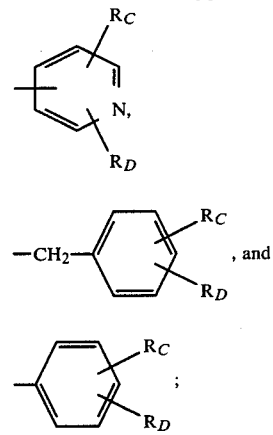
$R_B$ is selected from the group consisting of —straight or branched alkyl,
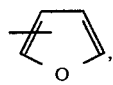
;
$R_C$ is selected from the group consisting of —H and —halogen; and
$R_D$ is selected from the group consisting of —H, —lower alkyl, —lower alkoxyl, —halogen, and —CF$_3$.
21 Claims, No Drawings

IMIDAZOLE PLANT GROWTH REGULATORS

This invention is in the field of heterocyclic organic chemical compounds; more specifically, those nitrogenous compounds known as imidazoles, especially substituted imidazoles, as well as agricultural compositions containing substituted imidazoles and the method of their use to regulate the growth of plants.

Many organic chemicals affect the growth of plants. More often than not, application of an organic chemical to plants has a detrimental effect, including death of the plants. Such chemicals are referred to as herbicides. Occasionally compounds are discovered which have beneficial effects on plants, but are not simply nutrient-supplying fertilizers. Such beneficial effects include increasing the yield of fruit, seeds, fiber, or other plant products. Another beneficial effect may be an increase in the nutritional value of food products derived from the plants. It is a beneficial effect of some compounds to facilitate harvesting the plant product. Yet another beneficial effect in certain cases is an increase in the storage life of the plant product. Such non-nutrient chemical compounds which are beneficial to plants in small amounts are referred to as plant growth regulators.

As used herein, the term "plant growth regulator" means a chemical compound which, when applied in the recommended manner, modifies the normal growth of a plant. Such modifications may include, but are not limited to: root initiation; set, development, ripening and abscission of fruits; plant size and shape; suppression of lodging; control of axillary buds and lateral shoots; metabolism regulation, including senescence; breaking or enforcing dormancy in seeds, buds, and storage organs; promotion or delay of flowering; defoliation; desiccation; and growth promotion under stress. Although a plant growth regulator, as that term is used herein, may inhibit plant growth even when the compound is properly used, the term does not contemplate total growth inhibition or killing the plant when the regulator is used as recommended.

The plant growth regulating compounds of this invention are substituted imidazoles. Imidazole itself is best represented by the following tautomeric structures:

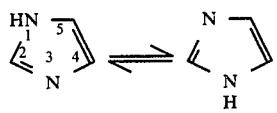

Because of the indicated proton shift, the 4- and 5-positions of the 1H-imidazole ring are indistinguishable.

Biological effects on plants, including both herbicidal and plant growth regulator activity, have been attributed to variously substituted imidazole compounds. For example, UK patent application No. 2 084 140, published Apr. 7, 1982, discloses generically that certain benzamide-substituted imidazoles are herbicides, and U.S. Pat. No. 3,261,873 discloses that 2-halo imidazoles with additional 4- and 5-substitution are herbicides.

According to DDR Pat. No. 140 966, published Apr. 9, 1980, certain substituted imidazolecarboxylic acid anilides are plant growth regulators. These anilides are reported to be antilodging agents in grains, suitable for determining sex in cucumbers, increasing the fruit set in tomatoes, inhibiting sucker formation in tobacco and tomatoes, and affecting flowering and dwarfing in asters.

Cytokinin-like activity has been attributed to N-phenyl-1H-imidazole-4-carboxamide as the result of a tobacco callus bioassay ("Proceedings of Eighth International Conference on Plant Growth Substances," K. V. Thimann, Editor, Hirokawa, Tokyo, Japan, 1974, pages 447–455). Structure-activity relationships of cytokinins have been reviewed by Matsubara, *Phytochemistry* 19, 2239-53 (1980).

It has now been found that a series of imidazole derivatives carrying substituents other than hydrogen in either or both the 4- and 5-positions are plant growth regulators. Some of the substituted imidazoles are new compounds. The compounds per se and compositions including the substituted imidazoles and adapted for agricultural use are within the scope of this invention.

Plants exposed to the subject compounds display a spectrum of growth regulator responses; e.g., the substituted imidazoles exhibit cytokinin-like activity in promoting the growth of tobacco callus and delaying the senescence of plants. The methods of using the substituted imidazoles for controlling the growth and delaying the senescence of plants are also within the scope of this invention.

The instant invention utilizes substituted imidazoles of the formula

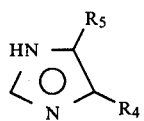

wherein $R_4$ is selected from the group consisting of —H, —lower alkyl, —NO$_2$, —CN, and —CONHY; and $R_5$ is selected from the group consisting of —NZ-COR$_A$, —CONZR$_B$, —COOZ, —Cl, —Br, —CN, —NO$_2$,

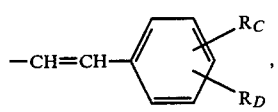

—NHZ,

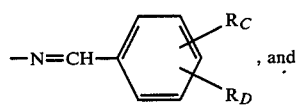

, and

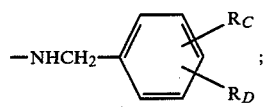

;

in which

Y is selected from the group consisting of —H, —lower alkyl, —aryl, and —substituted aryl;

Z is selected from the group consisting of —H and —lower alkyl;

$R_A$ is selected from the group consisting of —straight or branched alkyl, —lower alkoxyl,

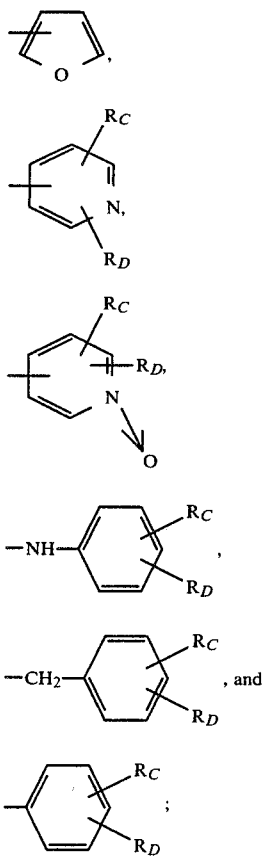

$R_B$ is selected from the group consisting of —straight or branched alkyl,

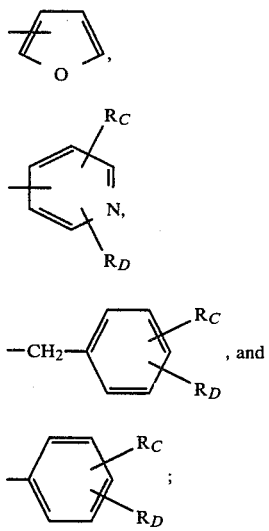

$R_C$ is selected from the group consisting of —H and —halogen; and $R_D$ is selected from the group consisting of —H, —lower alkyl, —lower alkoxyl, —halogen, and —CF$_3$.

In the aforesaid description and wherever employed in this application the terms "halogen" or "halo" mean fluorine, chlorine and bromine. Similarly, the term "lower alkyl" means a straight or branched chain containing 1 to 6, preferably 1 to 4, carbon atoms, and the term "lower alkoxyl" contemplates bonded to oxygen a straight or branched chain containing 1 to 6, preferably 1 to 4 carbon atoms.

Among the substituted imidazoles embraced by the aforesaid description, those in which R$_4$ is other than —CONHY are preferred, especially those compounds in which R$_4$ is —CN. When R$_4$ is —CN, the substituted imidazoles of greatest interest are those in which R$_5$ is selected from —NHCOR$_A$, —CONHR$_B$ and —NHCH$_2$—, wherein R$_A$ or R$_B$ is alkyl, phenyl, halophenyl, phenylmethyl, pyridinyl, or furanyl. Specific substituted imidazoles of this type which are of greatest interest are N-(5-cyano-1H-imidazol-4-yl)pentanamide, N-(5-cyano-1H-imidazol-4-yl)benzamide, N-(5-cyano-1H-imidazol-4-yl)-3-chlorobenzamide, N-(5-cyano-1H-imidazol-4-yl)-3-fluorobenzamide, N-(5-cyano-1H-imidazol-4-yl)-4-fluorobenzamide, N-(5-cyano-1H-imidazol-4-yl)-3-methylbenzamide, N-(5-cyano-1H-imidazol-4-yl)phenylacetamide, 5-cyano-4-phenylmethylamino-1H-imidazole, N-(5-cyano-1H-imidazol-4-yl)-4-chlorobenzamide, N-(5-cyano-1H-imidazol-4-yl)-4-bromobenzamide, N-(5-cyano-1H-imidazol-4-yl)-4-pyridinecarboxamide, and N-(5-cyano-1H-imidazol-4-yl)-2-furancarboxamide. Among the aforesaid specific compounds, the first eight named are preferred, and N-(5-cyano-1H-imidazol-4-yl)benzamide displays outstanding plant growth regulator activity.

Substituted imidazoles in which R$_4$ is —H or lower alkyl, e.g., methyl, are also useful. Compounds of this type which are especially attractive are N-phenyl-5-methyl-1H-imidazole-4-carboxamide, N-(3-fluorophenyl)-5-methyl-1H-imidazole-4-carboxamide, N-(3-chlorophenyl)-5-methyl-1H-imidazole-4-carboxamide, and N-(3-fluorophenyl)-1H-imidazole-4-carboxamide, the first three compounds named being of greatest interest.

The substituted imidazoles of this invention can be prepared by known methods. Useful synthesis intermediates include 4-amino-1H-imidazole-5-carbonitrile, which can be prepared by the method of Ferris and Orgel, J. Am. Chem. Soc., 88, 3829–3831 (1966), and 4-amino-5-imidazolecarboxamide hydrochloride, which is available in commerce. Representative syntheses of substituted imidazoles are set forth in the following Examples. In the Examples, temperatures are in degrees Celsius, NMR spectra were obtained in DMSO unless stated otherwise, and the chemical shifts of the lines are reported in ppm relative to tetramethylsilane as an internal standard.

EXAMPLE 1

N-(5-Cyano-1H-imidazol-4-yl)-3-fluorobenzamide

Under a nitrogen atmosphere a stirred solution of 4-amino-1H-imidazole-5-carbonitrile (1.1 g, 0.01 mole) and 3-fluorobenzoyl chloride (1.8 g, 0.011 mole) in 25 ml of dry pyridine was heated at reflux for one hour. The reaction mixture was cooled and the pyridine removed under reduced pressure. The residue was washed with saturated aqueous sodium bicarbonate and water. The residual solid was collected by filtration and washed sequentially with two portions of water, diethyl ether, and ethyl acetate. The solid was dried under reduced pressure; mp, 222°–240°. The solid was dissolved in ethanol and precipitated with petroleum ether, then collected by filtration and washed with diethyl ether to give after drying N-(5-cyano-1H-imidazol-4-yl)-3-fluorobenzamide (2.0 g; mp, 242°–46°).

The nmr and ir spectra were consistent with the proposed structure.

nmr: 7.77(m,4H); 7.9(s,1H); 11.3(bs,1H); 12.9(bs,1H).

EXAMPLE 2

N-(5-Cyano-1H-imidazol-4-yl)-4-pyridinecarboxamide N-oxide

To a stirred suspension of N-(5-cyano-1H-imidazol-4-yl)-4-pyridinecarboxamide (0.53 g, 0.0025 mole), which can be made by the procedure of Example 1 substituting isonicotinoyl chloride for the 3-fluorobenzoyl chloride, in 20 ml of ethyl acetate was added 3-chloroperbenzoic acid (0.65 g, 0.003 mole). The mixture was heated at reflux for 15 hours, cooled and the solid product collected by filtration. The solid was washed with ethyl acetate and dried under reduced pressure to give N-(5-cyano-1H-imidazol-4-yl)-4-pyridinecarboxamide N-oxide (0.52 g; mp, 290°).

The nmr and ir spectra were consistent with the proposed structure.

Analysis: Calc'd for $C_{10}H_7N_5O_2$: C 52.40; H 3.08; N 30.56; Found: C 53.80; H 3.17; N 30.73.

nmr (in trifluoroacetic acid, 2 protons exchanged): 8.47–9.47(m,5H).

EXAMPLE 3

N-Phenyl-N'-(5-cyano-1H-imidazol-4-yl)urea

Under a nitrogen atmosphere a stirred solution of 4-amino-1H-imidazole-5-carbonitrile (1.1 g, 0.01 mole) and phenyl isocyanate (1.3 g, 0.011 mole) in 30 ml of dry methyl ethyl ketone was heated under reflux for 10 hours. The solvent was removed, and the residue was stirred with 50 ml of boiling tetrahydrofuran. The mixture was filtered hot, and the filtrate was concentrated under reduced pressure. The residual solid was slurried in 50 ml of diethyl ether and the solid was collected by filtration, washed three times with diethyl ether, and dried to give a solid (1.2 g; mp, 165° d). The solid was dissolved in hot ethanol/toluene and an insoluble material removed by filtration. The filtrate was concentrated under reduced pressure to give N-phenyl-N'-(5-cyano-1H-imidazol-4-yl)urea (0.93 g; mp, >300°).

The nmr spectrum was consistent with the proposed structure.

nmr: 7.5(m,6H); 8.83(bs,1H); 9.23(bs,1H); 9.7(bs,1H).

EXAMPLE 4

5-(3-Fluorobenzoylamino)-1H-imidazole-4-carboxamide

This compound was prepared in the manner of Example 1 substituting 4-amino-5-imidazolecarboxamide hydrochloride (1.7 g, 0.01 mole) for the 4-amino-1H-imidazole-5-carbonitrile. The solid reaction product was recrystallized from ethanol to give 5-(3-fluorobenzoylamino)-1H-imidazole-4-carboxamide (1.2 g; mp, 243°–245°).

The nmr spectrum was consistent with the proposed structure.

nmr: 7.6(s,1H); 7.7(m,7H); 11.26(bs,1H).

EXAMPLE 5

N-(3-Fluorophenyl)-1H-imidazole-4-carboxamide

A stirred solution of 4,5-imidazoledicarboxylic acid (20.0 g, 0.128 mole) and 750 ml of acetic anhydride was heated under reflux for five hours. The reaction mixture was then cooled and filtered. The residue was taken up in 300 ml of water and the mixture heated on a steam bath for 30 minutes. Ethanol was added and the solution heated an additional 30 minutes on the steam bath. Decolorizing carbon was added, and the mixture was flitered hot through diatomaceous earth. The filtrate was refrigerated for 16 hours and the solid 4-imidazolecarboxylic acid precipitate collected by filtration.

A stirred solution of 4-imidazolecarboxylic acid (1.1 g, 0.01 mole) in 10 ml of thionyl chloride was heated at reflux under dry nitrogen for 16 hours. The excess thionyl chloride was removed by codistillation with 5 ml aliquots of toluene. Pyridine, 10 ml, and 3-fluoroaniline (1.1 g, 0.01 mole) were added to the residual acid chloride and the stirred reaction mixture heated under reflux for two hours. The reaction mixture was concentrated under reduced pressure. The residue was slurried with aqueous saturated sodium bicarbonate. The resultant solid was collected by filtration and washed sequentially with water and diethyl ether. The solid was dried under reduced pressure to give N-(3-fluorophenyl)-1H-imidazole-4-carboxyamide; (1.2 g; mp, 200°–206°).

Analysis: Calc'd for $C_{10}H_8FN_3O$: C 58.54; H 3.93; N 20.48; Found: C 58.47; H 3.86; N 20.09.

nmr: 6.8–8.1 (bm,6H); 10.3 (s,2H).

EXAMPLE 6

N-(3-Chlorophenyl)-5-methyl-1H-imidazole-4-carboxamide

Sodium hydroxide (70.0 g, 1.75 moles), followed by ethyl 5-methyl-1H-imidazole-4-carboxylate (34.0 g, 0.22 mole), were added to 500 ml of water. The reaction mixture was stirred and heated at reflux for one hour, cooled in an ice bath, and neutralized with 150 ml of concentrated hydrochloric acid. The precipitated solid was collected and dried to give 5-methyl-1H-imidazole-4-carboxylic acid.

Under a dry nitrogen atmosphere, a stirred suspension of 5-methyl-1H-imidazole-4-carboxylic acid (12.6 g, 0.10 mole) and several drops of dimethylformamide in 125 ml of dry tetrahydrofuran was cooled in an ice bath. Oxalyl chloride, 20 ml, in 50 ml of tetrahydrofuran was carefully added dropwise. Upon complete addition the reaction mixture was heated under reflux for two hours, cooled to ambient temperature and diluted with 100 ml of diethyl ether. A solid precipitated and was collected by filtration, washed with diethyl ether, and dried to give 5-methyl-1H-imidazole-4-carboxylic acid chloride.

Under a dry nitrogen atmosphere a solution of 5-methyl-1H-imidazole-4-carboxylic acid chloride (1.5 g, 0.01 mole) and 3-chloroaniline (1.3 g, 0.01 mole) in 25 ml of pyridine was stirred at ambient temperature for two days. The reaction mixture was then concentrated under reduced pressure, and the residue was slurried with aqueous saturated sodium bicarbonate. The resultant solid was collected by filtration, washed with water, and recrystallized, yielding N-(3-chlorophenyl)-5-methyl-1H-imidazole-4-carboxamide; (0.5 g; mp, 199°–202°).

Analysis: Calc'd for $C_{11}H_{10}ClN_3O$: C 56.06; H 4.28; N 17.83; Found: C 55.31; H 4.16; N 17.38 nmr: 2.7(s,3H); 3.4(b,1H); 6.9–8.7(m,5H); 9.9(bs,1H).

EXAMPLE 7

5-Cyano-4-phenylmethylamino-1H-imidazole

To a stirred solution of 4-amino-1H-imidazol-5-carbonitrile (1.1 g, 0.01 mole) in 25 ml of methanol was added 1.1 grams of benzaldehyde. The reaction mixture was then stirred at ambient temperature for 16 hours, heated on a steam bath for 20 minutes, cooled to ambient temperature, then stirred with 25 ml of diethyl ether. The mixture was filtered and the filtrate concentrated under reduced pressure to a residual solid. The solid was recrystallized from toluene-butanol to give 5-cyano-4-phenylmethylimino-1H-imidazole (0.92 g; mp, 200°–202°).

Analysis: Calc'd for $C_{11}H_8N_4$: C 67.33; H 4.11; N 28.56 Found: C 66.94; H 3.98; N 28.74

To a stirred solution of 5-cyano-4-phenylmethylimino-1H-imidazole (0.7 g, 0.004 mole) in 10 ml of methanol was added 5 ml of a 1M sodium acetate/acetic acid buffer (pH=6), followed by sodium cyanoborohydride (0.5 g, 0.008 mole). The pH of the reaction mixture was adjusted to 6 by the dropwise addition of acetic acid. The reaction mixture was stirred at ambient temperature for 17 hours, and the pH was adjusted to 10 with aqueous 5% sodium hydroxide. The pH of the reaction mixture was readjusted to 6 with aqueous 2N hydrochloric acid and the mixture extracted with four 50 ml portions of diethyl ether. The combined yellow extracts were dried with magnesium sulfate and filtered. The filtrate was concentrated under reduced pressure to a residual oil. The oil was chromatographed on a column using silica gel as the stationary phase and diethyl ether as the eluant, to give 5-cyano-4-phenylmethylamino-1H-imidazole (0.24 g; mp, 95°–97°).

Analysis: Calc'd for $C_{11}H_{10}N_4$: C 66.64; H 5.09; N 28.27 Found: C 66.40; H 5.13; N 28.21 nmr: 4.5(d,2H); 7.0(bt,1H); 7.9(s,5H); 11.9(bs,1H).

The substituted imidazoles of Examples 1–7, together with other exemplary members of the series prepared by similar methods, are listed along with their melting points in Table I. The new compounds were also characterized by elemental analyses as well as infrared and nuclear magnetic resonance spectra.

In the normal use of the aforesaid substituted imidazole plant growth regulators, the active compounds usually will not be employed free from admixture or dilution, but ordinarily will be used in a suitable formulated agricultural composition compatible with the method of application and comprising a plant growth regulant effective amount of at least one of said active compounds. Said substituted imidazole compounds, like most pesticidal agents, may be blended with the agriculturally acceptable surface-active agents and carriers normally employed for facilitating the dispersion of active ingredients, recognizing the accepted fact that the formulation and mode of application of a plant growth regulator may affect the activity of the material. The present active compounds may be applied, for example, as sprays, dusts, or granules to the area where plant growth regulation is desired, the type of application varying of course with the plant and the environment. Thus, the substituted imidazole compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said active compounds. The granule particles are relatively large, a diameter of about 400–2500 microns typically. The particles are either impregnated with the active compound from solution or coated with the compound, adhesive sometimes being employed. Granules generally contain 0.05–20% by weight, preferably 0.5–5%, active ingredient as the plant growth regulant effective amount. A typical granular formulation employed for evaluation purposes contains 95% attapulgite clay (24/48 mesh) and 5% N-(5-cyano-1H-imidazol-4-yl)benzamide.

Dusts are admixtures of said active compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the plant growth regulator. These finely divided solids have an average particle size of less than about 50 microns. A typical dust formulation useful for regulating plant growth contains by weight 5 parts N-(3-fluoro)phenyl-1H-imidazole-4-carboxamide and 95 parts talc.

The substituted imidazole compounds of the present invention may be made into liquid concentrates by dissolution or emulsification in suitable liquids and into solid concentrates by admixture with talc, clays, and other known solid carriers used in the pesticide art. The concentrates are compositions containing, as a growth regulant effective amount, about 5–50% the substituted imidazole by weight and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are avilable in commerce. The surface-active agent, when used, normally comprises about 1–15% by weight of the plant growth regulator composition.

Other useful formulations include simple solutions of the active ingredient in a solvent in which it is completely soluble at the desired concentration, such as acetone or other organic solvents.

A plant growth regulant effective amount of said substituted imidazole in a plant growth regulator composition diluted for application is normally in the range of about 0.004% to about 5% by weight. Many variations of spraying and dusting compositions known in the art may be used by substituting said plant growth regulator compounds of this invention into compositions known or apparent to the art. The plant growth regulator compositions of this invention may be formulated with other active ingredients, including insecticides, nematicides, acaricides, fungicides, other plant growth regulators, fertilizers, etc.

In using the compositions to regulate plant growth, including delay of senescence, according to the method of this invention, it is only necessary that a plant growth regulant effective amount or senescence delaying effective amount of at least one of said substituted imidazoles be applied to the locus where regulation or senescence delay is desired, generally a soil locus where agricultural crops are grown and either before or, preferably, after the plants have emerged. Liquid plant growth regulator compositions may be incorporated into the soil, applied to the soil as a drench, or sprayed on the foliage of growing plants. Solid compositions may be applied by broadcasting or in bands. For most applications, a plant growth regulant effective amount, or senescence delaying effective amount, will be about 0.1 to 8 kg, preferably 0.1 to 2 kg, per hectare.

The plant growth regulators of this invention were investigated for activity in preemergence and postemergence tests according to the following procedure:

Flats were filled with a steam-sterilized sandy loam soil. Seeds of the following test plant species were planted in furrows: cotton (*Gossypium hirsutum*) or limabean (*Phaseolus limensis*), field corn (*Zea mays L.*), soybean (*Glycine max*), wheat (*Triticum aestivum*), barnyardgrass (*Echinochloa crus galli*), johnsongrass (*Sorghum halepense*), pitted morningglory (*Ipomoea lacunosa*), velvetleaf (*Abutilon theophriasti*), field bindweed (*Convolvulus arvenia*), and green foxtail (*Setaria viridis*). Soil was leveled to a 1 cm depth over the seeds.

In both the preemergence and postemergence tests the test chemicals were applied as aqueous acetone solutions at a rate equivalent to 8.0 kilograms/hectare.

A flat for preemergence test was watered and the soil evenly drenched with the water-acetone solution of test chemical. The treated flat was placed in a greenhouse where it was watered regularly at the soil surface for a period of 13 days. The effect of the test chemical was then recorded. In some tests individual plant species were examined for percent kill and a vigor rating of one to five was assigned to the surviving plants, a vigor of five signifying no chemical injury. In other tests percent kill and vigor rating were combined in a single rating called "percent control," which has the following significance:

| Percent Control | Description of Effect | Effect on Crops | Effect on Weeds |
|---|---|---|---|
| 0 | No effect | No crop reduction | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop injury no recovery | Moderate weed control |
| 70 | | Heavy injury and stand loss | Control somewhat less than satisfactory |
| 80 | Severe effect | Crop nearly destroyed a few survivors | Satisfactory to good weed control |
| 90 | | Only occasional live plants left | Very good to excellent control |
| 100 | Completely effective | Complete crop destruction | Complete weed destruction |

Footnotes denoting other morphological responses observed were also recorded.

A flat for postemergence test was placed in a greenhouse for an 8 to 10 day growing period. The test solution was then hand-sprayed onto the foliage of the emerged test plants. After spraying, the foliage of the test plants was kept dry for 24 hours after which time regular watering was resumed for a period of 13 days. The effect of the test chemical was then recorded in the same manner described for the preemergence tests.

The results of the preemergence and postemergence tests appear in Tables II and III, respectively. In the Tables, columns headed "PC," "V," "K," and "F" refer to percent control, vigor, kill, and footnotes, respectively. Footnotes B, C, D, E, G, H, J, M, P, Q, and U, defined in the Tables and described in more detail below, indicate plant growth regulator activity.

Stunting (footnote B) can retard the growth of grasses, which reduces maintenance time for lawns, golf courses, and highway rights-of-way. Stunting in fruit trees may reduce stem growth, which can reduce pruning and trimming time. Stunting in cereal and broadleaf crops such as wheat, cotton, and soybeans may result in a shorter, thicker stalk which resists lodging, in turn promoting higher yields.

Desiccation (footnote C) can reduce the pre-harvest moisture content in cereals such as wheat, or in broadleaf crops such as sunflower. Desiccation can result in the loss of foliage, and in such plants as soybeans, cotton, peanuts, and potatoes the loss of foliage aids in harvesting.

Axillary growth stimulation (footnote D), or branching, can lead to multiple stems in cereals such as wheat (tillering). An increase in the number of stems may increase the yield. In soybeans, axillary stimulation at flowering can result in more fruits, increasing yield.

Nastic response (footnote E) is manifested by twisting and bending of the plants and indicates a hormonal disruption. A natural and useful nastic response is the curling of a tendril or stem around a support, e.g., in peas and pole beans.

Stimulation (footnote G) of vegetative growth in crops such as clover results in increased yields of forage. The stimulation of reproductive growth in fruits and cereals will also result in increased yields from those crops.

Defoliation (footnote H), or loss of plant foliage just prior to harvesting crops such as soybeans, cotton, peanuts and potatoes will facilitate harvest of those crops. Foliage present at the time cotton is harvested may stain the cotton.

Intumescence (footnote J) indicates formation of abnormal swellings, a disruption of the hormonal balance that promotes normal growth. Intumescence-causing agents can promote the growth of tissue, such as tobacco callus.

Negative root geotropism (footnote M) connotes the upward growth of roots out of the soil and indicates disruption of the plant's normal hormonal balance. There can be a correlation between negative root geotropism and increase in the number of pods on soybean plants.

Deeper green lower leaves (footnote P) suggests delay of senescence, increased chlorophyll production, or chlorophyll retention. These phenomena mean greater photosynthesis, which may increase yield from plants such as soybeans.

Leaf alteration (footnote Q) indicates disruption in the plant's hormonal balance. Leaves of plants can be altered to allow better utilization of sunlight, which may enhance plant growth.

A number of the substituted imidazoles of this invention were also evaluated for antisenescence activity, indicated by footnote P, according to the following procedure:

The substituted imidazoles were tested for their ability to cause the chlorophyll present to be retained in excised wheat leaves as compared to frozen wheat leaf controls, which were assumed to retain 100% of their chlorophyll. Thus, wheat leaves were excised, weighed, and either frozen or placed in a vial containing water or a water-acetone solution of either a test chemical or kinetin, a known antisenescence agent, at concentrations equal to or less than $10^{-5}M$. After four days at 30° in the dark, the chlorophyll content of the excised leaves was measured by extracting the chlorophyll from the leaves with methanol. The absorbance of the chlorophyll-containing extracts was determined at 652 nm, a strong chlorophyll absorption band, and used to determine the amount of chlorophyll retained in the treated excised leaves compared with the frozen wheat leaf control from which the chlorophyll was similarly extracted. The results of these tests are presented in Table IV.

The substituted imidazoles were also evaluated for their ability to increase the yield of food product from soybeans by delaying senescence of the plants. N-(5-cyano-1H-imidazol-4-yl)benzamide was sprayed as a water:acetone solution containing 0.1% (v/v) sorbitan monolaurate at rates of 0.125–2.0 kg active/ha on soybeans at various stages of growth, i.e., at reproductive stages $R_4$, $R_5$, or $R_6$, as defined by Fehr and Caviness, Special Report 80, Iowa State University, Ames, Iowa 50011, February 1979. Each group of soybean test plants was assessed for leaf and/or pod senescence on a weekly basis beginning approximately 14 days following treatment. The soybean test plants were maintained in a growth chamber until they reached full maturity. The soybean test plants were then assessed for yield. The results are given in Tables V and VI. Application at the $R_5$ or $R_6$ stage led to a significant delay in senescence.

TABLE I
Substituted Imidazoles

| Example | Name | MP °C. |
|---|---|---|
| 1 | N—(5-cyano-1H—imidazol-4-yl)-3-fluorobenzamide | 242–6 |
| 2 | N—(5-cyano-1H—imidazol-4-yl)-4-pyridinecarboxamide N—oxide | 290 |
| 3 | N—phenyl-N'—(5-cyano-1H—imidazol-4-yl)urea | >300 |
| 4 | 4-(3-fluorobenzoylamino)-1H—imidazole-5-carboxamide | 243–5 |
| 5 | N—(3-fluorophenyl)-1H—imidazole-4-carboxamide | 200–6 |
| 6 | N—(3-chlorophenyl)-5-methyl-1H—imidazole-4-carboxamide | 199–202 |
| 7 | 5-cyano-4-phenylmethylamino-1H—imidazole | 95–7 |
| 8 | N—(5-cyano-1H—imidazol-4-yl)-pentanamide | 187–9 |
| 9 | methyl (5-cyano-1H—imidazol-4-yl)carbamate | >300 |
| 10 | N—(5-cyano-1H—imidazol-4-yl)-benzamide | 226–30 |
| 11 | N—(5-cyano-1H—imidazol-4-yl)-2-chlorobenzamide | 215–17 |
| 12 | N—(5-cyano-1H—imidazol-4-yl)-3-chlorobenzamide | 246–9 |
| 13 | N—(5-cyano-1H—imidazol-4-yl)-4-chlorobenzamide | 265–8 |
| 14 | N—(5-cyano-1H—imidazol-4-yl)-4-bromobenzamide | 265 d |
| 15 | N—(5-cyano-1H—imidazol-4-yl)-2-fluorobenzamide | 171 d |
| 16 | N—(5-cyano-1H—imidazol-4-yl)-4-fluorobenzamide | 258–62 |
| 17 | N—(5-cyano-1H—imidazol-4-yl)-3,4-dichlorobenzamide | 244 d |
| 18 | N—(5-cyano-1H—imidazol-4-yl)-3-methylbenzamide | 217–21 |
| 19 | N—(5-cyano-1H—imidazol-4-yl)-4-methylbenzamide | 225 d |
| 20 | N—(5-cyano-1H—imidazol-4-yl)-3-trifluoromethylbenzamide | 205–8 |
| 21 | N—(5-cyano-1H—imidazol-4-yl)-4-trifluoromethylbenzamide | 230 d |
| 22 | N—(5-cyano-1H—imidazol-4-yl)-4-methoxybenzamide | 256 d |
| 23 | N—(5-cyano-1H—imidazol-4-yl)-4-pyridinecarboxamide | >300 |
| 24 | N—(5-cyano-1H—imidazol-4-yl)-(2-chloro-4-pyridine)carboxamide | 247 |
| 25 | N—(5-cyano-1H—imidazol-4-yl)-2-furancarboxamide | >300 |
| 26 | N—(5-cyano-1H—imidazol-4-yl)-phenylacetamide | 201–4 |
| 27 | N—(3-fluorophenyl)-N'—(5-cyano-1H—imidazol-4-yl-urea | >300 |
| 28 | 4-benzoylamino-1H—imidazole-5-carboxamide | 241–3 |
| 29 | N—(5-cyano-1H—imidazole-4-yl)-2-bromobenzamide | 187–91 |
| 30 | N—(5-cyano-1H—imidazol-4-yl)-2-methylbenzamide | 146–7 |
| 31 | N—(5-cyano-1H—imidazol-4-yl)-2-trifluoromethylbenzamide | 210–13 |
| 32 | 4-pentanoylamino-1H—imidazole-5-carboxamide | 176–80 |
| 33 | N—phenyl-5-methyl-1H—imidazole-4-carboxamide | 230 d |
| 34 | N—(2-chlorophenyl)-5-methyl-1H—imidazole-4-carboxamide | 193–7 |
| 35 | N—(4-chlorophenyl)-4-methyl-1H—imidazole-4-carboxamide | 160 d |

TABLE I-continued

Substituted Imidazoles

| Example | Name | MP °C. |
|---------|------|--------|
| 36 | N—(3-fluorophenyl)-5-methyl-1H—imidazole-4-carboxamide | 220 |
| 37 | N—phenyl-5-cyano-1H—imidazole-4-carboxamide | 206 d |
| 38 | N—(3-fluorophenyl)-5-cyano-1H—imidazole-4-carboxamide | 180 d |
| 39 | N—(4-pyridinyl)-5-cyano-1H—imidazole-4-carboxamide | 280 d |
| 40 | N—(4-methylphenyl)-5-methyl-1H—imidazole-4-carboxamide | 192-5 |
| 41 | N—(2-fluorophenyl))-5-methyl-1H—imidazole-4-carboxamide | 264 d |
| 42 | N—(3,4-dichlorophenyl)-5-methyl-1H—imidazole-4-carboxamide | 193-5 |
| 43 | N—(4-fluorophenyl-5-methyl-1H—imidazole-4-carboxamide | 209-11 |
| 44 | N—(3-chlorophenyl)-1H—imidazole-4-carboxamide | 198-200 |
| 45 | N—(4-methoxyphenyl)-1H—imidazole-4-carboxamide | 219-222 |
| 46 | N—(3,4-dichlorophenyl)-1H—imidazole-4-carboxamide | 225-7 |
| 47 | N—(2-fluorophenyl)-1H—imidazole-4-carboxamide | 187-9 |
| 48 | N—(2-chlorophenyl)-1H—imidazole-4-carboxamide | 195-7 |
| 49 | N—(3-trifluoromethylphenyl)-1H—imidazole-4-carboxamide | 171-3 |
| 50 | N—(4-fluorophenyl)-1H—imidazole-4-carboxamide | 249-51 |
| 51 | N—(4-trifluoromethylphenyl)-1H—imidazole-4-carboxamide | 211-13 |
| 52 | 5-cyano-1H—imidazole-4-carboxylic acid, methyl ester | 168-71 |
| 53 | 5-cyano-1H—imidazole-4-carboxylic acid, ethyl ester | 167-71 |
| 54 | 4-bromo-1H—imidazole | 129-32 |
| 55 | 5-bromo-4-nitro-1H—imidazole | 228 |
| 56 | 5-methyl-4-nitro-1H—imidazole | 234 |
| 57 | 4,5-dinitro-1H—imidazole | 182-3 |
| 58 | 4-amino-1H—imidazole-5-carbonitrile | 123-6 |
| 59 | 4-chloro-5-nitro-1H—imidazole | 240-5 |
| 60 | 5-cyano-4 phenylmethylamino-1H—imidazole | 200-2 |

TABLE II

Preemergence Tests

Plant

| Example | Barngr V | K | PC or F | Bindweed V | K | PC or F | Corn-F V | K | PC or F | Greenfox V | K | PC or F | Johngr V | K | PC or F | Cotton¹ Lima Bean V | K | PC or F | Mrnglory V | K | PC or F | Soybean V | K | PC or F | Velvetlf V | K | PC or F | Wheat V | K | PC or F |
|---|---|---|---|---|---|---|---|---|---|---|---|---|---|---|---|---|---|---|---|---|---|---|---|---|---|---|---|---|---|---|
| 1 | 3 | 0 | AB | 3 | 30 | ABI | 3 | 30 | AB | 3 | 0 | AB | 3 | 0 | AB | 3 | 0 | B | 3 | 0 | ABI | 3 | 0 | B | 0 | 100 | 0 | 3 | 0 | ABE |
| 2 | 4 | 0 | A | 4 | 0 | 0 | 4 | 0 | A | 4 | 0 | A | 4 | 0 | A | 4 | 0 | A | 4 | 0 | A | 4 | 0 | A | 5 | 0 | 0 | 4 | 0 | A |
| 4 | 4 | 0 | A | 5 | 0 | 0 | 4 | 0 | A | 4 | 0 | A | 4 | 0 | A | 5 | 0 | 0 | 4 | 0 | A | 4 | 0 | 0 | 5 | 0 | 0 | 4 | 0 | A |
| 5 | 4 | 0 | AP | 4 | 0 | 0 | 4 | 0 | 0 | 4 | 30 | AB B3 | 0 | 0 | 0 | 0 | 0 | 0 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 8 | 4 | 0 | AP | 4 | 0 | 0 | 4 | 0 | AQ | 4 | 0 | A | 4 | 0 | AB | 4 | 0 | BE | 4 | 0 | A | 4 | 0 | AI | 4 | 1Q | A | 0 | 0 | AB |
| 9 | 5 | 0 | B | 5 | 0 | 0 | 5 | 0 | ABEIP | 5 | 0 | A | 5 | 0 | BE | 5 | 50 | 0 | 5 | 10 | BI | 5 | 0 | A | 5 | 0 | 0 | 5 | 0 | 0 |
| 10 | 4 | 0 | AB | 4 | 0 | A | 4 | 0 | A | 4 | 0 | A | 4 | 0 | A | 4 | 0 | ABI¹ | 4 | 0 | A | 4 | 0 | A | 4 | 0 | BI | 4 | 10 | ABEI |
| 11 | 4 | 0 | AB | 4 | 40 | AB | 4 | 0 | ABQ | 4 | 0 | AB | 4 | 0 | AB | 5 | 0 | AI | 4 | 0 | BI | 4 | 30 | BDEIP | 4 | 0 | 0 | 4 | 0 | A |
| 12 | 3 | 0 | AB | 3 | 20 | AB | 3 | 0 | ABEQ | 3 | 20 | AB | 3 | 0 | AB | 3 | 0 | B | 3 | 0 | A | 3 | 20 | A | 3 | 0 | AB | 3 | 20 | AB |
| 13 | 4 | 0 | AB | 4 | 0 | AB | 4 | 0 | EIQ | 4 | 0 | 0 | 4 | 0 | BE | 4 | 0 | AI¹ | 4 | 0 | AB | 4 | 10 | AB | 4 | 0 | B | 4 | 10 | AB |
| 14 | 3 | 0 | 0 | 5 | 0 | AI | 5 | 0 | AQ | 5 | 0 | A | 5 | 0 | 0 | 5 | 0 | AB¹ | 5 | 0 | I | 5 | 0 | ABEI | 5 | 0 | IN | 5 | 0 | 0 |
| 15 | 5 | 0 | AB | 3 | 20 | ABI | 3 | 0 | ABEIPQ | 3 | 0 | AB | 3 | 0 | ABE | 2 | 90 | ABEI¹ | 3 | 0 | B | 3 | 0 | BEI | 3 | 0 | ABI | 4 | 0 | BEP |
| 16 | 3 | 0 | AB | 4 | 0 | AIN | 4 | 0 | A | 4 | 0 | A | 4 | 0 | AB | 5 | 0 | ABI¹ | 4 | 0 | I | 4 | 0 | 0 | 4 | 0 | AIN | 4 | 0 | A |
| 17 | 4 | 0 | AB | 3 | 30 | ABN | 3 | 0 | ABEIQ | 3 | 0 | BN | 3 | 0 | ABE | 3 | 0 | ABEI¹ | 3 | 0 | BI | 3 | 0 | B | 4 | 0 | BI | 4 | 0 | ABEP |
| 18 | 5 | 0 | ABE | 5 | 70 | 0 | 5 | 30 | AQ | 5 | 0 | A | 5 | 0 | AB | 3 | 0 | BEI 3 | 4 | 30 | B | 4 | 0 | ABEI | 4 | 50 | AIN | 5 | 0 | 0 |
| 19 | 3 | 0 | A | 4 | 0 | AI | 4 | 30 | AB | 4 | 0 | AI | 4 | 0 | 0 | 2 | 90 | 0¹ | ABIN 3 | 0 | ABIN 3 | 80 | ABI | 4 | 4 | 20 | AB | 5 | AB |
| 20 | 4 | 0 | AB | 4 | 0 | L | 4 | 0 | AQ | 4 | 0 | B | 4 | 0 | AB | 5 | 0 | 0 | 0 | 0 | ABN | 4 | 0 | 4 | 5 | 0 | 4 | 5 | 0 | 0 |
| 21 | 4 | 0 | A | 4 | 0 | A | 4 | 0 | 0 | 4 | 19 | AI | 4 | 0 | AB | 5 | 0 | 0¹ | 4 | 0 | L | 4 | 0 | ABEI | 5 | 0 | L | 5 | 0 | 0 |
| 22 | 4 | 0 | B | 5 | 0 | 0 | 5 | 0 | AB | 5 | 0 | AB | 5 | 0 | B | 5 | 100 | 0 | 5 | 0 | A | 4 | 0 | B | 5 | 0 | A | 5 | 0 | A |
| 23 | 4 | 0 | ABP | 4 | 0 | 0 | 4 | 0 | 0 | 4 | 0 | A | 4 | 0 | A | 4 | 0 | A¹ | 4 | 0 | B | 4 | 0 | 0 | 3 | 50 | AB | 4 | 0 | B |
| 24 | 4 | 0 | A | 5 | 0 | 0 | 5 | 0 | AB | 5 | 0 | A | 5 | 0 | B | 5 | 100 | 0¹ | 5 | 0 | B | 5 | 0 | AEI | 5 | 0 | 0 | 4 | 0 | A |
| 25 | 4 | 0 | A | 4 | 0 | 0 | 4 | 0 | EIQM | 4 | 0 | A | 4 | 0 | A | 4 | 0 | 0¹ | 4 | 0 | A | 4 | 0 | 0 | 4 | 0 | AB | 4 | 0 | BM |
| 26 | 4 | 0 | 0 | 5 | 0 | 0 | 5 | 0 | 0 | 5 | 0 | A | 5 | 0 | 0 | 5 | 0 | A¹ | 4 | 0 | AI | 4 | 0 | 0 | 3 | 0 | 0 | 5 | 0 | A |
| 27 | 4 | 0 | A | 4 | 0 | ABI | 4 | 0 | A | 4 | 0 | A | 4 | 0 | 0 | 4 | 0 | AB¹ | 4 | 0 | 0 | 4 | 0 | 0 | 4 | 0 | ABI | 4 | 0 | A |
| 28 | 5 | 0 | P | 5 | 0 | 0 | 5 | 30 | K | 5 | 0 | A | 5 | 0 | A | 4 | 0 | A¹ | 4 | 0 | A | 4 | 0 | F | 4 | 0 | 0 | 5 | 0 | A |
| 29 | 4 | 0 | 0 | 4 | 0 | 0 | 4 | 30 | K | 4 | 0 | A | 4 | 0 | B | 5 | 0 | AB | 5 | 0 | F | 5 | 0 | 0 | 5 | 0 | 0 | 5 | 0 | A |
| 30 | 5 | 0 | 0 | 5 | 0 | 0 | 5 | 70 | 0 | 5 | 0 | A | 5 | 0 | A | 4 | 0 | AB | 4 | 0 | AB | 4 | 0 | 0 | 4 | 0 | 0 | 4 | 0 | A |
| 31 | 4 | 0 | P | 4 | 0 | 0 | 4 | 0 | 0 | 4 | 0 | A | 4 | 0 | AB | 4 | 0 | A | 4 | 10 | AB | 4 | 0 | AB | 4 | 30 | AB | 4 | 0 | B |
| 32 | 3 | 0 | 0 | 5 | 0 | 0 | 5 | 30 | B | 5 | 0 | 0 | 5 | 0 | A | 4 | 0 | A | 4 | 0 | AB | 4 | 0 | ABI | 4 | 0 | AB | 4 | 0 | AB |
| 33 | 4 | 0 | 0 | 4 | 0 | 0 | 4 | 0 | 0 | 4 | 0 | A | 4 | 0 | AB | 3 | 0 | A | 3 | 0 | AB | 3 | 0 | I | 3 | 0 | A | 3 | 0 | A |
| 34 | 4 | 0 | AP | 4 | 20 | AB | 4 | 30 | 0 | 4 | 0 | A | 4 | 0 | A | 4 | 0 | AB | 4 | 0 | A | 4 | 0 | A | 4 | 0 | 0 | 4 | 0 | A |
| 35 | 4 | 0 | AB | 4 | 0 | B | 4 | 0 | 0 | 4 | 20 | AB | 4 | 0 | A | 4 | 0 | A | 4 | 0 | B | 4 | 0 | B | 4 | 0 | 0 | 4 | 0 | B2 |
| 36 | 5 | 0 | AB | 5 | 0 | AB | 5 | 0 | AB | 5 | 0 | AB | 5 | 0 | AB | 5 | 0 | AB | 5 | 0 | AB | 5 | 0 | ABI | 5 | 0 | AB | 0 | 0 | 0 |
| 37 | 3 | 0 | AP | 4 | 0 | AB | 4 | 0 | A | 4 | 0 | A | 4 | 0 | A | 3 | 0 | AB | 3 | 10 | AB | 3 | 0 | I | 3 | 0 | A | 0 | 0 | 0 |
| 38 | 40 | 0 | A | 4 | 0 | AB | 4 | 0 | 0 | 4 | 0 | A | 4 | 0 | A | 4 | 0 | A | 4 | 0 | B | 4 | 0 | B2 | 4 | 0 | B | 0 | 0 | 0 |
| 39 | 4 | 0 | A | 5 | 0 | 0 | 5 | 0 | 0 | 5 | 0 | A | 5 | 0 | AB2 | 4 | 0 | B2¹ | 4 | 0 | B | 4 | 0 | 0 | 4 | 0 | 0 | 4 | 0 | 0 |
| 40 | 5 | 0 | 0 | 5 | 0 | 0 | 5 | 0 | 0 | 5 | 0 | 0 | 5 | 0 | 0 | 4 | 0 | 0 | 4 | 0 | 0 | 4 | 0 | 0 | 4 | 0 | 0 | 4 | 0 | 0 |
| 41 | 4 | 0 | AB2P | 4 | 0 | 0 | 4 | 30 | AB2I | 4 | 0 | 0 | 4 | 0 | 0 | 4 | 0 | 0 | 4 | 0 | 0 | 4 | 0 | 0 | 4 | 0 | 0 | 0 | 0 | 0 |
| 42 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 43 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 44 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE II-continued

Preemergence Tests

| Example | Barngr V | Barngr K | Barngr F | Bindweed V | Bindweed K | Bindweed F | Corn-F V | Corn-F K | Corn-F F | Grenfox V | Grenfox K | Grenfox F | Johngr V | Johngr K | Johngr F | Cotton¹/Lima Bean V | Cotton¹/Lima Bean K | Cotton¹/Lima Bean F | Mrnglory V | Mrnglory K | Mrnglory F | Soybean V | Soybean K | Soybean F | Velvetlf V | Velvetlf K | Velvetlf F | Wheat V | Wheat K | Wheat F |
|---|---|---|---|---|---|---|---|---|---|---|---|---|---|---|---|---|---|---|---|---|---|---|---|---|---|---|---|---|---|---|
| 48 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 49 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 50 | 0 | 0 | B2 | 10 | 0 | B1 | 0 | 0 | B2 | 20 | 0 | B2 | 10 | 0 | B1 | 50 | 30 | B31 | 40 | 0 | BE2 | 80 | 0 | BSEI | 50 | 20 | B2 | 0 | 0 | 0 |
| 51 | 5 | 0 | 0 | 5 | 0 | 0 | 5 | 0 | B | 4 | 0 | N | 5 | 0 | 0 | 4 | 0 | B | 4 | 0 | I | 4 | 0 | B | 4 | 0 | ABI | 0 | 0 | 0 |
| 52 | 5 | 0 | 0 | 5 | 0 | 0 | 4 | 70 | K | 5 | 0 | 0 | 5 | 0 | 0 | 5 | 0 | A¹ | 5 | 0 | 0 | 4 | 0 | A | 5 | 0 | 0 | 0 | 0 | 0 |
| 53 | 5 | 0 | 0 | 5 | 0 | 0 | 5 | 0 | 0 | 5 | 0 | 0 | 5 | 0 | 0 | 5 | 0 | 0¹ | 5 | 0 | B | 5 | 0 | 0 | 5 | 0 | 0 | 0 | 0 | A |
| 54 | 5 | 0 | 0 | 5 | 0 | 0 | 5 | 0 | B | 5 | 0 | 0 | 5 | 0 | 0 | 5 | 0 | A¹ | 4 | 0 | 0 | 4 | 0 | A | 4 | 0 | E | 0 | 0 | 0 |
| 55 | 5 | 0 | 0 | 5 | 0 | 0 | 5 | 0 | 0 | 5 | 0 | 0 | 5 | 0 | 0 | 5 | 0 | 0¹ | 5 | 0 | B | 5 | 0 | 0 | 5 | 0 | 0 | 5 | 0 | 0 |
| 56 | 5 | 0 | 0 | 3 | 0 | 0 | 5 | 0 | B | 4 | 0 | A | 5 | 0 | 0 | 5 | 0 | A¹ | 5 | 0 | 0 | 4 | 0 | A | 4 | 0 | E | 4 | 0 | A |
| 57 | 5 | 0 | 0 | 5 | 0 | 0 | 5 | 0 | 0 | 4 | 0 | 0 | 5 | 0 | 0 | 5 | 0 | 0¹ | 5 | 0 | 0 | 5 | 0 | E | 5 | 0 | 0 | 5 | 0 | 0 |
| 58 | 5 | 0 | 0 | 5 | 0 | 0 | 5 | 0 | 0 | 4 | 0 | 0 | 5 | 0 | 0 | 5 | 0 | 0 | 5 | 0 | 0 | 5 | 0 | 0 | 5 | 0 | 0 | 5 | 0 | A |
| 59 | 5 | 0 | 0 | 3 | 4C | B1 | 4 | 0 | 1 | 4 | 0 | 0 | 5 | 0 | 0 | 3 | 0 | B1IN¹ | 3 | 50 | ABEI | 0 | 100 | 0 | 4 | 0 | 0 | 4 | 0 | A |
| 60 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

FOOTNOTES
V = Vigor
5 = Plants normal
4 = Slight injury; plants will or have already recovered
3 = Moderate injury; plants expected to recover
2 = Moderate to severe injury; plants are not expected to recover
1 = Severe injury; plants will not recover
0 = Dead plant
K = % Kill
F = Footnote:
A = Necrosis
B = Stunted
C = Desiccation
D = Axillary Growth Stimulation
E = Nastic Responses
F = Necrotic Spots
G = Growth Stimulation
H = Defoliant
I = Chlorosis
J = Intumescence
K = Suspected germination failure
L = Stand may be affected by non-chemical factors
M = Negative root geotropism
N = Bleaching
P = Deeper green lower leaves
Q = Leaf alterations
U = Any other morphological response
Sub-footnotes:
1 = 0%–24%
2 = 25%–49%
3 = 50%–74%
4 = 75%–100%
5 = refers to stunting only 75%–100% stunted with 0–30% phytotoxicity
¹Data for cotton

TABLE III

Postemergence Tests Plant

| Example | Barngr V | Barngr K | Barngr PC or F | Bindweed V | Bindweed K | Bindweed PC or F | Corn-F V | Corn-F K | Corn-F PC or F | Greenfox V | Greenfox K | Greenfox PC or F | Johngr V | Johngr K | Johngr PC or F | Cotton/Lima Bean V | Cotton/Lima Bean K | Cotton/Lima Bean PC or F[1] | Mrnglory V | Mrnglory K | Mrnglory PC or F | Soybean V | Soybean K | Soybean PC or F | Velvetlf V | Velvetlf K | Velvetlf PC or F | Wheat V | Wheat K | Wheat PC or F |
|---|---|---|---|---|---|---|---|---|---|---|---|---|---|---|---|---|---|---|---|---|---|---|---|---|---|---|---|---|---|---|
| 1 | 3 | 0 | AB | 4 | 0 | AI | 5 | 0 | 0 | 4 | 0 | A | 4 | 0 | A | 3 | 0 | ABEI | 4 | 0 | AI | 4 | 0 | ABDI | 2 | 30 | AB | 4 | 0 | A |
| 2 | 4 | 0 | C | 4 | 0 | CI | 4 | 0 | C | 4 | 0 | C | 0 | 0 | C | 4 | 0 | CI | 4 | 0 | BC | 4 | 0 | CI | 4 | 0 | CI | 4 | 0 | C |
| 3 | 5 | 0 | 0 | 5 | 0 | 0 | 4 | 0 | A | 4 | 30 | AB | 4 | 0 | A | 4 | 0 | AI | 5 | 0 | BC | 5 | 0 | 0 | 4 | 0 | A | 5 | 0 | 0 |
| 4 | 4 | 0 | A | 4 | 60 | A | 5 | 0 | C | 4 | 0 | B | 4 | 0 | C | 3 | 0 | CI | 4 | 0 | 0 | 4 | 0 | A | 4 | 0 | C | 4 | 0 | A |
| 5 | 4 | 0 | C | 3 | 0 | BC | 4 | 0 | C | 3 | 0 | A | 4 | 0 | A | 10 | 0 | A | 10 | 0 | BC | 10 | 10 | CE | 4 | 0 | 0 | 4 | 0 | C |
| 6 | 20 | 0 | A | 30 | 0 | AB2 | 10 | 0 | A | 10 | 0 | A | 20 | 0 | A | 30 | 0 | A | 10 | 0 | A | 30 | 0 | A | 10 | 0 | A | 10 | 0 | P |
| 7 | 30 | 0 | AB2 | 20 | 0 | A | 20 | 0 | AB1 | 10 | 0 | A | 20 | 0 | AB1 | 4 | 0 | AB1 | 4 | 0 | AB1 | 4 | 0 | AB1D | 10 | 0 | ABI | 4 | 0 | A |
| 8 | 4 | 0 | A | 4 | 0 | A | 4 | 0 | A | 4 | 0 | A | 4 | 0 | A | 4 | 0 | AI | 4 | 0 | A | 4 | 0 | AI | 4 | 0 | AB | 4 | 0 | A |
| 9 | 5 | 0 | 0 | 5 | 0 | 0 | 5 | 0 | 0 | 5 | 0 | 0 | 4 | 0 | 0 | 4 | 0 | A | 4 | 0 | A | 4 | 0 | A | 5 | 0 | A | 5 | 0 | A |
| 10 | 4 | 0 | AP | 4 | 30 | BI | 5 | 0 | A | 4 | 10 | A | 3 | 50 | AB | 3 | 0 | ABI | 4 | 0 | BN | 3 | 0 | ABDEI | 3 | 0 | ABI | 4 | 0 | 0 |
| 11 | 3 | 0 | AB | 4 | 10 | AB | 5 | 0 | A | 5 | 0 | A | 4 | 20 | A | 4 | 0 | A | 5 | 0 | A | 3 | 0 | AI | 5 | 0 | A | 5 | 0 | A |
| 12 | 4 | 0 | AB | 4 | 20 | BA | 5 | 0 | A | 4 | 90 | A | 3 | 50 | BA | 4 | 0 | AI | 3 | 10 | A | 3 | 0 | ABDEI | 4 | 0 | ABI | 4 | 0 | A |
| 13 | 4 | 0 | ABP | 4 | 0 | 0 | 4 | 0 | A | 3 | 10 | A | 4 | 0 | AB | 4 | 0 | AEI | 4 | 0 | AI | 3 | 0 | AI | 4 | 0 | AI | 4 | 0 | A |
| 14 | 4 | 0 | P | 4 | 30 | AB | 5 | 0 | B | 4 | 0 | BA | 4 | 0 | BA | 4 | 0 | ABE[1] | 5 | 0 | A | 5 | 0 | BADE | 5 | 0 | A | 5 | 0 | 0 |
| 15 | 4 | 0 | A | 3 | 10 | BA | 5 | 0 | A | 3 | 10 | A | 4 | 50 | AB | 4 | 70 | AM | 4 | 0 | 0 | 4 | 0 | AI | 4 | 0 | BA | 4 | 0 | A |
| 16 | 4 | 0 | P | 4 | 20 | BA | 5 | 0 | A | 2 | 90 | A | 3 | 20 | A | 4 | 0 | BA[1] | 5 | 0 | AB | 3 | 0 | BAEI | 3 | 100 | A | 4 | 0 | A |
| 17 | 4 | 0 | AP | 4 | 200 | 0 | 5 | 0 | A | 4 | 60 | A | 5 | 20 | AB | 4 | 0 | AI | 5 | 0 | A | 4 | 0 | ADI | 3 | 40 | ABI | 4 | 0 | A |
| 18 | 4 | 0 | P | 4 | 0 | A | 4 | 0 | A | 4 | 0 | A | 4 | 0 | A | 4 | 0 | BA[1] | 5 | 10 | AI | 4 | 0 | BI | 5 | 0 | AB | 5 | 0 | I |
| 19 | 4 | 0 | AP | 4 | 0 | AB | 4 | 0 | B | 4 | 40 | A | 4 | 0 | A | 4 | 0 | ABI | 4 | 0 | AI | 4 | 0 | I | 3 | 0 | 0 | 4 | 0 | A |
| 20 | 4 | 0 | AP | 4 | 0 | BI | 5 | 0 | A | 4 | 0 | A | 4 | 0 | A | 4 | 0 | AI | 4 | 10 | AIN | 3 | 0 | BADI | 5 | 0 | 0 | 5 | 0 | A |
| 21 | 4 | 0 | A | 4 | 0 | A | 5 | 0 | A | 4 | 0 | A | 4 | 0 | A | 4 | 0 | AI | 4 | 0 | I | 4 | 0 | AD | 5 | 0 | 0 | 5 | 0 | A |
| 22 | 4 | 0 | A | 4 | 0 | 0 | 5 | 0 | A | 4 | 0 | A | 4 | 0 | A | 4 | 0 | BA[1] | 5 | 0 | A | 4 | 0 | 0 | 4 | 0 | 0 | 4 | 0 | C |
| 23 | 4 | 0 | A | 4 | 0 | A | 5 | 0 | A | 5 | 0 | A | 4 | 0 | A | 4 | 0 | AI | 4 | 0 | A | 5 | 0 | A | 5 | 0 | 0 | 4 | 0 | AB |
| 24 | 5 | 0 | BC | 4 | 0 | C | 5 | 0 | BC | 4 | 0 | BC | 5 | 0 | BC | 5 | 0 | BCI[1] | 4 | 0 | BCI | 3 | 0 | BCD | 4 | 0 | BCI | 4 | 0 | C |
| 25 | 4 | 0 | A | 4 | 0 | AB | 5 | 0 | A | 4 | 0 | AB | 4 | 0 | A | 3 | 0 | AI[1] | 4 | 0 | A | 5 | 0 | ADEI | 4 | 0 | A | 5 | 0 | AB |
| 26 | 4 | 0 | A | 4 | 0 | A | 4 | 0 | A | 4 | 0 | A | 4 | 0 | A | 4 | 0 | AI | 5 | 0 | AIG | 5 | 0 | AEI | 4 | 0 | A | 4 | 0 | A |
| 27 | 4 | 0 | A | 4 | 0 | A | 4 | 0 | A | 4 | 0 | A | 4 | 0 | C | 4 | 0 | CI | 5 | 0 | BC | 4 | 0 | CI | 4 | 0 | BC | 4 | 0 | A |
| 28 | 5 | 0 | A | 5 | 0 | 0 | 4 | 0 | BC | 5 | 0 | 0 | 5 | 0 | 0 | 5 | 0 | 0 | 5 | 0 | 0 | 5 | 0 | 0 | 4 | 0 | A | 5 | 0 | 0 |
| 29 | 4 | 0 | A | 4 | 0 | A | 4 | 0 | A | 4 | 20 | A | 4 | 0 | A | 4 | 0 | AI | 4 | 0 | A | 4 | 0 | A | 4 | 0 | A | 4 | 0 | A |
| 30 | 5 | 0 | B1 | 5 | 0 | A | 4 | 0 | B2 | 4 | 0 | A | 5 | 0 | A | 4 | 0 | B1[1] | 5 | 0 | AB1 | 4 | 0 | FA | 5 | 0 | B1 | 4 | 0 | AB |
| 31 | 5 | 0 | B1 | 5 | 0 | B1 | 4 | 0 | B2 | 4 | 0 | A | 5 | 0 | 100 | 4 | 0 | 0[1] | 5 | 0 | C | 4 | 0 | ABIP | 4 | 0 | 0 | 4 | 0 | AB |
| 32 | 30 | 0 | AB1 | 20 | 0 | AB2I | 10 | 0 | A | 10 | 0 | A | 20 | 0 | A | 20 | 0 | A | 20 | 0 | AB1 | 20 | 0 | B1FP | 20 | 0 | ABI | 20 | 0 | AB1 |
| 33 | 4 | 0 | A | 5 | 0 | A | 5 | 0 | A | 5 | 0 | A | 4 | 0 | A | 5 | 0 | I | 5 | 0 | 0 | 4 | 0 | A | 5 | 0 | AB | 4 | 0 | 0 |
| 34 | 4 | 0 | A | 5 | 0 | 0 | 5 | 0 | A | 5 | 0 | A | 5 | 20 | A | 5 | 0 | A | 5 | 0 | 0 | 5 | 0 | 0 | 5 | 0 | 0 | 5 | 0 | 0 |
| 35 | 4 | 0 | C | 4 | 0 | C | 5 | 0 | C | 5 | 0 | 0 | 4 | 0 | C | 4 | 0 | CI | 5 | 0 | C | 5 | 0 | BCEI | 4 | 30 | BC | 4 | 0 | C |
| 36 | 4 | 0 | C | 5 | 0 | AB | 4 | 0 | A | 5 | 0 | BC | 4 | 0 | 0 | 5 | 0 | AI[1] | 5 | 0 | AIG | 5 | 0 | AEI | 4 | 10 | A | 4 | 0 | C |
| 37 | 4 | 0 | A | 4 | 0 | A | 4 | 0 | A | 5 | 0 | A | 4 | 0 | C | 4 | 0 | A | 4 | 0 | BC | 3 | 0 | CI | 4 | 0 | BC | 4 | 0 | A |
| 38 | 4 | 0 | A | 4 | 0 | 0 | 4 | 0 | A | 4 | 0 | A | 5 | 0 | A | 4 | 0 | CI | 5 | 0 | A | 4 | 0 | AI | 5 | 0 | AB | 4 | 0 | C |
| 39 | 4 | 0 | A | 4 | 0 | A | 4 | 0 | A | 4 | 0 | A | 4 | 0 | A | 4 | 0 | AI | 4 | 0 | A | 5 | 0 | AI | 4 | 0 | A | 5 | 0 | A |
| 40 | 4 | 0 | 0 | 5 | 0 | 0 | 4 | 0 | 0 | 5 | 0 | 0 | 5 | 0 | 0 | 4 | 0 | A | 5 | 0 | A | 4 | 0 | 0 | 4 | 0 | 0 | 4 | 0 | 0 |
| 41 | 4 | 10 | B1 | 5 | 0 | 0 | 4 | 0 | B1 | 4 | 0 | A | 5 | 0 | A | 5 | 0 | B1E[1] | 5 | 0 | AB2 | 4 | 0 | B2AP | 3 | 20 | B1 | 4 | 0 | B1A |
| 42 | 20 | 0 | A | 10 | 0 | A | 10 | 0 | A | 10 | 0 | A | 20 | 0 | A | 10 | 0 | 0[1] | 10 | 0 | A | 10 | 0 | ADI | 10 | 0 | A | 10 | 0 | A |
| 43 | 20 | 0 | AB1 | 10 | 0 | B1 | 20 | 0 | A | 10 | 0 | A | 20 | 0 | A | 10 | 0 | AB1 | 20 | 0 | AB2 | 20 | 0 | AI | 10 | 20 | B1 | 10 | 0 | A |
| 44 | 20 | 0 | AB1 | 30 | 0 | AB2I | 20 | 0 | AB1 | 10 | 0 | A | 20 | 0 | A | 10 | 0 | A | 30 | 0 | AB1 | 40 | 0 | AB2EI | 20 | 0 | AB1 | 20 | 0 | AB1 |
| 45 | 20 | 0 | A | 30 | 0 | A | 10 | 0 | AB1 | 10 | 0 | A | 20 | 0 | A | 10 | 0 | A | 20 | 0 | AB1 | 20 | 0 | AEI | 20 | 30 | A | 20 | 0 | A |
| 46 | 20 | 0 | A | 50 | 0 | AB2 | 30 | 0 | AB2 | 10 | 0 | AB | 20 | 0 | A | 10 | 0 | A | 30 | 0 | AB3 | 20 | 0 | AB1 | 10 | 0 | AB1 | 30 | 0 | AB1 |

TABLE III-continued

Postemergence Tests
Plant

| Example | Barngr V | Barngr K | Barngr PC or F | Bindweed V | Bindweed K | Bindweed PC or F | Corn-F V | Corn-F K | Corn-F PC or F | Greenfox V | Greenfox K | Greenfox PC or F | Johngr V | Johngr K | Johngr PC or F | Cotton[1] Lima Bean V | Cotton[1] Lima Bean K | Cotton[1] Lima Bean PC or F | Mrnglory V | Mrnglory K | Mrnglory PC or F | Soybean V | Soybean K | Soybean PC or F | Velvetlf V | Velvetlf K | Velvetlf PC or F | Wheat V | Wheat K | Wheat PC or F |
|---|---|---|---|---|---|---|---|---|---|---|---|---|---|---|---|---|---|---|---|---|---|---|---|---|---|---|---|---|---|---|
| 47 | 30 |  | AB1 | 30 |  | A | 10 |  | A | 30 |  | A | 30 |  | AB1 | 30 |  | AB1 | 30 |  | AB2EI | 60 |  | AB3DEI | 30 |  | AB2 | 30 |  | A |
| 48 | 30 |  | B1C2 | 10 |  | C1 | 10 |  | C1 | 10 |  | B1C1 | 30 |  | B1C2 | 10 |  | C1 | 30 |  | B2C1 | 70 |  | B3C3DEI | 30 |  | B2C1 | 30 |  | B1C1 |
| 49 | 20 |  | A | 60 |  | AB1H3 | 20 |  | A | 20 |  | AB1 | 20 |  | A | 10 |  | A | 20 |  | AB2I | 20 |  | AI | 20 |  | AB1 | 20 |  | A |
| 50 | 30 |  | AB2 | 30 |  | AB1 | 50 |  | AB3 | 10 |  | A | 20 |  | AB1 | 20 |  | AB1 | 20 |  | AB2 | 30 |  | AB2I | 10 |  | AB1 | 10 |  | A |
| 51 | 30 |  | A | 30 |  | AN | 0 |  | 0 | 30 |  | A | 20 |  | A | 30 |  | A | 20 |  | A | 20 |  | AFH1N | 30 |  | A | 30 |  | A |
| 52 | 5 |  | 0 | 4 |  | A | 5 |  | 0 | 4 |  | A | 5 |  | 0 | 4 |  | A | 4 |  | A | 4 |  | AI | 5 |  | 0 | 5 |  | 0 |
| 53 | 4 |  | A | 4 |  | A | 0 |  | AB | 4 |  | AB | 5 |  | C | 3 |  | AI | 4 |  | A | 4 |  | AI | 4 |  | 0 | 4 |  | A |
| 54 | 4 |  | C | 4 | 20 | C1 | 5 |  | 0 | 5 |  | C | 4 |  | 0 | 4 |  | CI[1] | 5 |  | C | 4 |  | CI | 5 | 30 | CI | 5 |  | 0 |
| 55 | 4 |  | 0 | 4 |  | C1 | 4 |  | 0 | 4 |  | 0 | 5 |  | 0 | 4 |  | CI[1] | 4 |  | 0 | 4 |  | CI | 3 |  | 0 | 5 |  | 0 |
| 56 | 5 |  | 0 | 4 |  | C1 | 4 |  | 0 | 4 |  | 0 | 5 |  | 0 | 4 |  | CI[1] | 4 | 0 | C | 4 |  | CI | 4 |  | CI | 5 |  | 0 |
| 57 | 4 |  | BC | 4 |  | C1 | 5 |  | 0 | 4 |  | C | 3 | 30 | BC | 4 |  | BCI[1] | 4 | 0 | BC | 4 |  | CI | 5 |  | 0 | 5 |  | 0 |
| 58 | 5 |  | 0 | 3 | 80 | AC | 4 |  | 0 | 5 |  | 0 | 5 |  | 0 | 2 | 90 | C | 4 | 20 | C | 3 |  | C | 3 | 40 | B2C1 | 4 |  | B1C1 |
| 59 | 3 | 20 | C1B2 | 3 | 30 | B1C1 | 4 |  | B2C1 | 5 |  | 0 | 5 | 10 | B2C2 | 4 |  | B4C[1] | 20 |  | B2C1 | 20 |  | B4C |  |  |  |  |  |  |
| 60 | 20 |  | A | 10 |  | A | 10 |  | AK | 30 |  | A | 10 |  | A | 20 |  | AB2 | 20 |  | AB2 | 20 |  | AEI | 20 |  | AB2 | 20 |  | AB1 |

FOOTNOTES
V = Vigor
5 = Plants normal
4 = Slight injury; plants will or have already recovered
3 = Moderate injury; plants expected to recover
2 = Moderate to severe injury; plants are not expected to recover
1 = Severe injury; plants will not recover
0 = Dead plant
K = % Kill
A = Necrosis
B = Stunted
C = Desiccation
D = Axillary Growth Stimulation
E = Nastic Responses
F = Necrotic Spots
G = Growth Stimulation
H = Defoliant
I = Chlorosis
J = Intumescence
K = Suspected germination failure
L = Stand may be affected by non-chemical factors
M = Negative root geotropism
N = Bleaching
P = Deeper green lower leaves
Q = Leaf alterations
U = Any other morphological response
Sub-footnotes:
1 = 0%–24%
2 = 25%–49%
3 = 50%–74%
4 = 75%–100%
5 = refers to stunting only
75%–100% stunted with 0–30% phytotoxicity
[1] Data for cotton

TABLE IV

Antisenescence Activity

| Example | Conc'n (M.) | Chlorophyll Retained (%) |
|---|---|---|
| Kinetin | $10^{-5}$ | 49.4 |
|  | $10^{-7}$ | 51.5 |
| H$_2$O | — | 11.3 |
| Frozen Wheat Leaf | — | 100 |
| 1 | $10^{-5}$ | 78.9 |
|  | $10^{-7}$ | 64.2 |
|  | $10^{-9}$ | 33.6 |
| 2 | $10^{-5}$ | 55.6 |
|  | $10^{-7}$ | 15.6 |
| 3 | $10^{-5}$ | 28.7 |
|  | $10^{-7}$ | 12.2 |
|  | $10^{-9}$ | 14.9 |
| 4 | $10^{-5}$ | 39.6 |
|  | $10^{-7}$ | 14.8 |
|  | $10^{-9}$ | 11.6 |
| 5 | $10^{-5}$ | 47.8 |
|  | $10^{-7}$ | 28.8 |
| 6 | $10^{-5}$ | 5 |
|  | $10^{-7}$ | 20 |
| 7 | $10^{-5}$ | 40 |
|  | $10^{-7}$ | 14 |
| 8 | $10^{-5}$ | 68.1 |
|  | $10^{-7}$ | 18.8 |
| 10 | $10^{-5}$ | 83.0 |
|  |  | 93.0 |
|  | $3 \times 10^{-6}$ | 89.9 |
|  | $10^{-6}$ | 90.0 |
|  | $3 \times 10^{-7}$ | 88.0 |
|  | $10^{-7}$ | 63.0 |
|  |  | 50.0 |
|  | $10^{-8}$ | 21.0 |
|  | $10^{-9}$ | 13.0 |
|  |  | 8.0 |
| 11 | $10^{-5}$ | 45.7 |
|  | $10^{-7}$ | 21.6 |
| 12 | $10^{-5}$ | 76.5 |
|  | $10^{-7}$ | 70.4 |
| 13 | $10^{-5}$ | 91.5 |
|  | $10^{-7}$ | 63.5 |
| 14 | $10^{-5}$ | 59 |
|  | $10^{-7}$ | 23 |
| 15 | $10^{-5}$ | 61.6 |
|  | $10^{-7}$ | 25.7 |
| 16 | $10^{-5}$ | 57.4 |
|  | $10^{-7}$ | 54.2 |
| 17 | $10^{-5}$ | 35.4 |
|  | $10^{-7}$ | 27.2 |
| 18 | $10^{-5}$ | 64.1 |
|  | $10^{-7}$ | 39.9 |
| 19 | $10^{-5}$ | 35.1 |
|  | $10^{-7}$ | 17.8 |
| 20 | $10^{-5}$ | 27.6 |
|  | $10^{-7}$ | 27.2 |
| 21 | $10^{-5}$ | 9 |
|  | $10^{-7}$ | 11 |
| 22 | $10^{-5}$ | 75.0 |
|  | $10^{-7}$ | 24.3 |
| 23 | $10^{-5}$ | 71.6 |
|  | $10^{-7}$ | 26.6 |
| 24 | $10^{-5}$ | 48.2 |
|  | $10^{-7}$ | 20.6 |
| 25 | $10^{-5}$ | 54.4 |
|  | $10^{-7}$ | 19.1 |
| 26 | $10^{-5}$ | 58.0 |
|  | $10^{-7}$ | 30.1 |
| 27 | $10^{-5}$ | 25.1 |
|  | $10^{-7}$ | 9.1 |
|  | $10^{-9}$ | 11.9 |
| 28 | $10^{-5}$ | 28.4 |
|  | $10^{-7}$ | 15.7 |
|  | $10^{-9}$ | 17.1 |
| 32 | $10^{-5}$ | 6 |
|  | $10^{-7}$ | 7 |
| 33 | $10^{-5}$ | 62.9 |
|  | $10^{-7}$ | 24.7 |
| 34 | $10^{-5}$ | 64 |
|  | $10^{-7}$ | 40 |
| 35 | $10^{-5}$ | 29.7 |
|  | $10^{-7}$ | 15.6 |
| 36 | $10^{-5}$ | 55.3 |
|  | $10^{-7}$ | 27.6 |
| 37 | $10^{-5}$ | 34.7 |
|  | $10^{-7}$ | 20.3 |
| 38 | $10^{-5}$ | 26.1 |
|  | $10^{-7}$ | 18.1 |
| 39 | $10^{-5}$ | 19.8 |
|  | $10^{-7}$ | 17.6 |
| 43 | $10^{-5}$ | 49 |
|  | $10^{-7}$ | 13 |
| 44 | $10^{-5}$ | 36 |
|  | $10^{-7}$ | 9 |
| 45 | $10^{-5}$ | 11 |
|  | $10^{-7}$ | 8 |
| 46 | $10^{-5}$ | 17 |
|  | $10^{-7}$ | 8 |
| 49 | $10^{-5}$ | 19 |
|  | $10^{-7}$ | 8 |
| 50 | $10^{-5}$ | 24 |
|  | $10^{-7}$ | 13 |
| 51 | $10^{-5}$ | 6 |
|  | $10^{-7}$ | 7 |
| 52 | $10^{-4}$ | 38.0 |
|  | $10^{-5}$ | 29.0 |
| 53 | $10^{-4}$ | 36.0 |
|  | $10^{-5}$ | 25.0 |
| 54 | $10^{-5}$ | 18.8 |
|  | $10^{-7}$ | 15.6 |
| 55 | $10^{-5}$ | 19.8 |
|  | $10^{-7}$ | 19.9 |
| 56 | $10^{-5}$ | 30.7 |
|  | $10^{-7}$ | 18.9 |
| 57 | $10^{-5}$ | 22.0 |
|  | $10^{-7}$ | 15.5 |
| 58 | $10^{-5}$ | 14.0 |
|  | $10^{-7}$ | 16.0 |
|  | $10^{-9}$ | 13.0 |

TABLE V

DELAY OF SOYBEAN LEAF AND POD SENESCENCE

| Reproductive Stage of Plant Development when treated | Water/Acetone Solution | Rate of Application | Leaf Senescence Delay (days) | Pod Senescence Delay (days) |
|---|---|---|---|---|
| R4 | 1:1 - water:acetone | 0.5 kg/ha | 1 | 2 |
| R5 | 1:1 - water:acetone | 2.0 | 5 | 2 |
| R5 | 4:1 - water:acetone | 1.0 | 10 | 4 |
| R6 | 1:1 - water:acetone | 2.0 | 6 | 5 |
| R6 | 4:1 - water: | 1.0 | 6 | 6 |

TABLE VI

| Reproductive Stage when sprayed | Water/Acetone Solution | Rate of Application | SOYBEAN YIELD Total Number of Pods | Total Number of Seeds | Total Weight of Seeds | Weight of 100 Seeds |
|---|---|---|---|---|---|---|
| R4 | 1:1 - water: acetone | 0.0 kg/ha | 54.4 | 134.4 | 20.8 grams | 15.7 grams |
| | | 0.125 | 53.6 | 133.4 | 20.8 | 16.0 |
| | | 0.50 | 58.4 | 145.3 | 20.0 | 14.1 |
| | | 2.0 | 49.0 | 112.8 | 17.0 | 15.0 |
| R5 | 1:1 - water: acetone | 0.0 | 47.4 | 115.8 | 16.6 | 14.8 |
| | | 0.125 | 48.2 | 109.8 | 16.6 | 13.0 |
| | | 0.50 | 48.8 | 111.8 | 13.9 | .14.1 |
| | | 2.0 | 46.4 | 105.3 | 15.7 | 15.7 |
| R5 | 4:1 - water: acetone | 0.0 | 52.2 | 119.4 | 13.2 | 13.6 |
| | | 0.125 | 58.2 | 134.0 | 17.8 | 13.5 |
| | | 0.50 | 51.8 | 124.8 | 20.0 | 13.0 |
| | | 1.0 | 55.0 | 129.5 | 18.7 | 14.6 |
| R6 | 1:1 - water: acetone | 0.0 | 56.0 | 130.2 | 17.9 | 13.9 |
| | | 0.125 | 48.6 | 112.0 | 15.3 | 13.9 |
| | | 0.50 | 51.8 | 127.4 | 17.5 | 14.3 |
| | | 2.0 | 56.8 | 139.4 | 21.2 | 15.4 |
| R6 | 4:1 - water: acetone | 0.0 | 54.2 | 123.2 | 16.8 | 13.9 |
| | | 0.125 | 57.4 | 130.2 | 18.7 | 14.7 |
| | | 0.50 | 54.0 | 129.6 | 17.9 | 14.2 |
| | | 1.0 | 51.8 | 130.2 | 21.5 | 16.6 |

What is claimed is:

1. Plant growth regulating substituted imidazoles of the formula

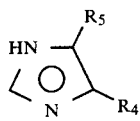

wherein $R_4$ is selected from the group consisting of —H, —lower alkyl, —CN, and —CONHZ; and $R_5$ is selected from the group consisting of —NZ-$COR_A$, —$CONZR_B$,

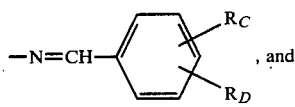, and

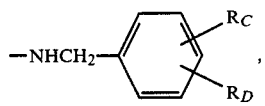, provided $R_4$ is —CN;

in which

Z is selected from the group consisting of —H and —lower alkyl;

$R_A$ is selected from the group consisting of —straight or branched (C$_2$-C$_8$) alkyl provided R$_4$ is other than —CONHZ,

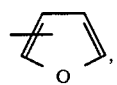

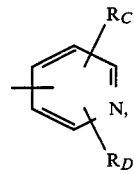

-continued

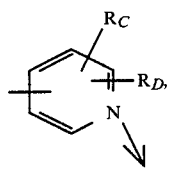

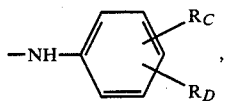

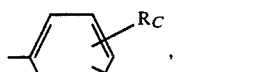, and

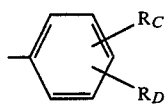

provided $R_4$, $R_C$ and $R_D$ are other than —H or —lower alkyl;

$R_B$ is selected from the group consisting of —straight or branched alkyl, provided R$_4$ is other than —CN, —H or —lower alkyl,

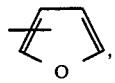

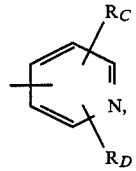

-continued

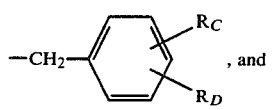, and

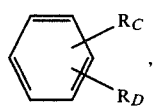, provided R₄ is other than —H or —lower alkyl;
R_C is selected from the group consisting of —H provided R₅ is other than

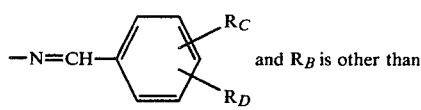 and R_B is other than

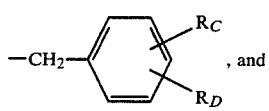, and and —halogen; and
R_D is selected from the group consisting of —H, —lower alkyl, —lower alkoxyl, —halogen, and —CF₃.

2. A substituted imidazole of claim 1 wherein R₄ is —CN.

3. A substituted imidazole of claim 2 wherein R₅ is selected from

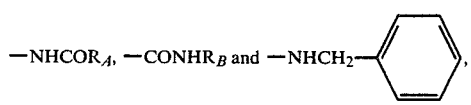

wherein R_A or R_B is alkyl, phenyl, halophenyl, phenylmethyl, pyridinyl, or furanyl.

4. A substituted imidazole of claim 1 selected from N-(5-cyano-1H-imidazol-4-yl)pentanamide, N-(5-cyano-1H-imidazol-4-yl)-3-chlorobenzamide, N-(5-cyano-1H-imidazol-4-yl)-3-fluorobenzamide, N-(5-cyano-1H-imidazol-4-yl)-4-fluorobenzamide, N-(5-cyano-1H-imidazol-4-yl)phenylacetamide, 5-cyano-4-phenylmethylamino-1H-imidazole, N-(5-cyano-1H-imidazol-4-yl)-4-chlorobenzamide, N-(5-cyano-1H-imidazol-4-yl)-4-bromobenzamide, N-(5-cyano-1H-imidazol-4-yl)-4-pyridinecarboxamide, and N-(5-cyano-1H-imidazol-4-yl)-2-furancarboxamide.

5. Plant growth regulator compositions comprising in admixture with an agriculturally acceptable carrier a plant growth regulant effective amount of at least one substituted imidazole of the formula

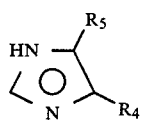

wherein

R₄ is selected from the group consisting of —H, —lower alkyl, —NO₂, —CN, and —CONHZ provided R₅ is other than

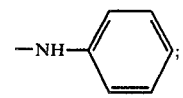;

and
R₅ is selected from the group consisting of —NZ-COR_A, —CONZR_B, —COOZ,

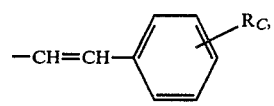

—NHZ provided R₄ is other than —CONHZ,

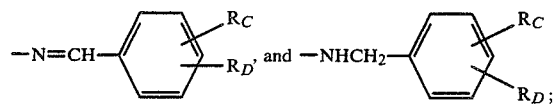;

in which
Z is selected from the group consisting of —H, provided R₅ is other than —COOZ, and —lower alkyl;
R_A is selected from the group consisting of —straight or branched alkyl provided R₄ is other than —CONHZ,

,

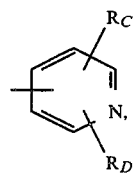

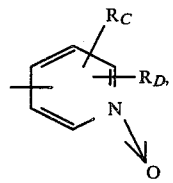

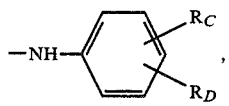,

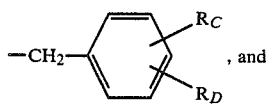, and

, provided R₄ is other than —H or —lower alkyl;
R_B is selected from the group consisting of —straight or branched alkyl provided R₄ is other than —CN, —H or —lower alkyl

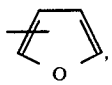

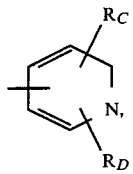

, and

, provided R₄ is other than —H or —lower alkyl;
R_C is selected from the group consisting of —H provided R₅ is other than

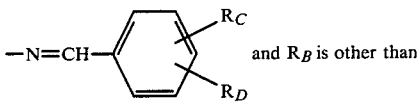 and R_B is other than

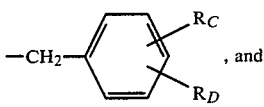, and

—halogen; and
R_D is selected from the group consisting of —H, —lower alkyl, —lower alkoxyl, —halogen, and —CF₃.

6. A composition of claim 5 wherein R₄ is —CN.
7. A composition of claim 6 wherein R₅ is selected from —NHCOR_A, —CONHR_B and 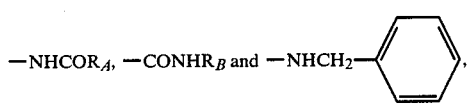, wherein R_A or R_B is alkyl, phenyl, halophenyl, phenylmethyl, pyridinyl, or furanyl.

8. A composition of claim 6 wherein said substituted imidazole is selected from N-(5-cyano-1H-imidazol-4-yl)pentanamide, N-(5-cyano-1H-imidazol-4-yl)benzamide, N-(5-cyano-1H-imidazol-4-yl)-3-chlorobenzamide, N-(5-cyano-1H-imidazol-4-yl)-3-fluorobenzamide, N-(5-cyano-1H-imidazol-4-yl)-4-fluorobenzamide, N-(5-cyano-1H-imidazol-4-yl)-3-methylbenzamide, N-(5-cyano-1H-imidazol-4-yl)phenylacetamide, 5-cyano-4-phenylmethylamino-1H-imidazole, N-(5-cyano-1H-imidazol-4-yl)-4-chlorobenzamide, N-(5-cyano-1H-imidazol-4-yl)-4-bromobenzamide, N-(5-cyano-1H-imidazol-4-yl)-4-pyridinecarboxamide, and N-(5-cyano-1H-imidazol-4-yl)-2-furancarboxamide.

9. The composition of claim 5 wherein said substituted imidazole is N-(5-cyano-1H-imidazol-4-yl)benzamide.

10. A method for regulating the growth of plants which comprises applying to the locus where regulation is desired a plant growth regulant effective amount of at least one substituted imidazole of the formula

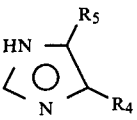

wherein
R₄ is selected from the group consisting of —H, —lower alkyl, —NO₂, —CN, and —CONHZ, provided R₅ is other than —CN; and
R₅ is selected from the group consisting of —NZCOR_A, —CONZR_B, —COOZ, —Cl, —Br, —CN, —NO₂,

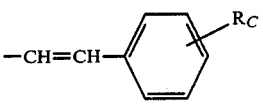,

—NHZ,

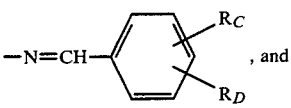, and

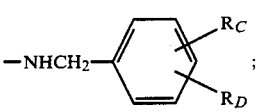;

in which
Z is selected from the group consisting of —H, provided R₅ is other than —COOZ, and —lower alkyl;
R_A is selected from the group consisting of —straight or branched alkyl, —lower alkoxyl,

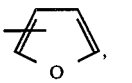,

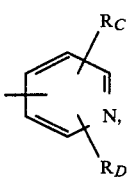

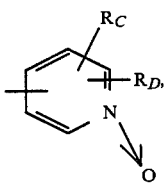

-continued

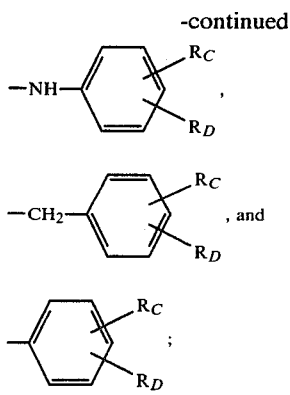

$R_B$ is selected from the group consisting of —straight or branched alkyl,

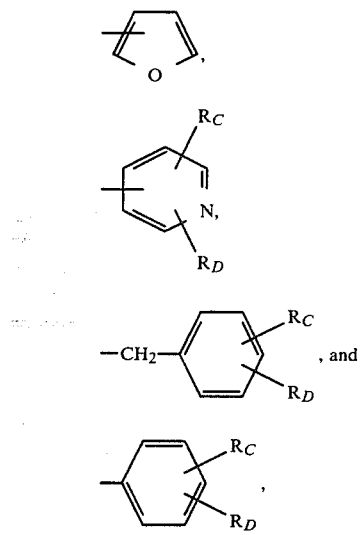

provided $R_4$ is other than —H or —lower alkyl;
$R_C$ is selected from the group consisting of —H and —halogen; and
$R_D$ is selected from the group consisting of —H, —lower alkyl, —lower alkoxyl, —halogen, and —CF$_3$.

11. The method of claim 10 wherein $R_4$ is —CN.

12. The method of claim 11 wherein $R_5$ is selected from

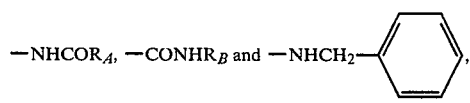

wherein $R_A$ or $R_B$ is alkyl, phenyl, halophenyl, phenylmethyl, pyridinyl, or furanyl.

13. The method of claim 10 wherein said substituted imidazole is selected from N-(5-cyano-1H-imidazol-4-yl)pentanamide, N-(5-cyano-1H-imidazol-4-yl)benzamide, N-(5-cyano-1H-imidazol-4-yl)-3-chlorobenzamide, N-(5-cyano-1H-imidazol-4-yl)-3-fluorobenzamide, N-(5-cyano-1H-imidazol-4-yl)-4-fluorobenzamide, N-(5-cyano-1H-imidazol-4-yl)-3-methylbenzamide, N-(5-cyano-1H-imidazol-4-yl)phenylacetamide, 5-cyano-4-phenylmethylamino-1H-imidazole, N-(5-cyano-1H-imidazol-4-yl)-4-chlorobenzamide, N-(5-cyano-1H-imidazol-4-yl)-4-bromobenzamide, N-(5-cyano-1H-imidazol-4-yl)-4-pyridinecarboxamide, and N-(5-cyano-1H-imidazol-4-yl)-2-furancarboxamide.

14. The method of claim 10 wherein said substituted imidazole is N-(5-cyano-1H-imidazol-4-yl)benzamide.

15. A method for delaying the senescence of plants which comprises applying to the locus where senescence delay is desired a senescence delaying effective amount of at least one substituted imidazole of the formula

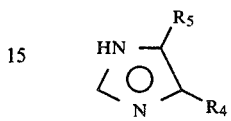

wherein
$R_4$ is selected from the group consisting of —H, —lower alkyl, —NO$_2$, —CN, and —CONHZ, provided $R_5$ is other than —CN; and
$R_5$ is selected from the group consisting of —NZ-COR$_A$, —CONZR$_B$, —COOZ, —Cl, —Br, provided $R_4$ is other than —H, —CN, —NO$_2$,

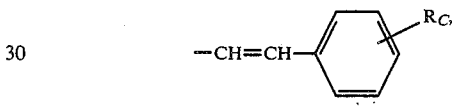

—NHZ, provided $R_4$ is other than —CN,

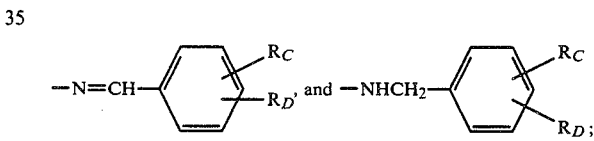

in which
Z is selected from the group consisting of —H, provided $R_5$ is other than —COOZ, and —lower alkyl;
$R_A$ is selected from the group consisting of —straight or branched alkyl, provided $R_4$ is other than —CONHZ, —lower alkoxyl,

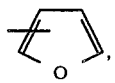

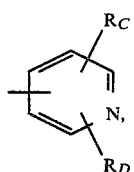

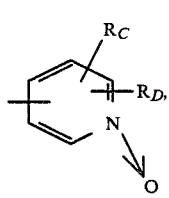

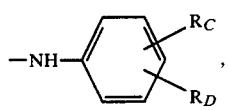

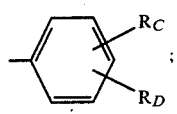

$R_B$ is selected from the group consisting of —straight or branched alkyl,

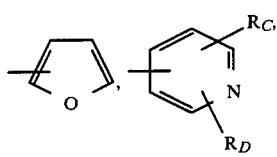

provided $R_4$ is other than —CN,

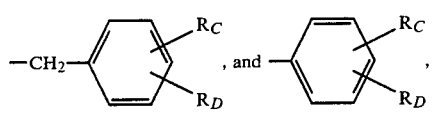

provided $R_4$ is other than —H or —lower alkyl;

$R_C$ is selected from the group consisting of —H and —halogen;

$R_D$ is selected from the group consisting of —H, —lower alkyl, —lower alkoxyl, —halogen, and —CF$_3$, other than 3—CF$_3$ when $R_4$ is —CN.

16. The method of claim 15 wherein $R_4$ is —CN.

17. The method of claim 16 wherein $R_5$ is selected from

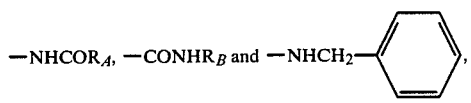

wherein $R_A$ or $R_B$ is alkyl, phenyl, halophenyl, phenylmethyl, pyridinyl, or furanyl.

18. The method of claim 15 wherein said substituted imidazole is selected from N-(5-cyano-1H-imidazol-4-yl)pentanamide, N-(5-cyano-1H-imidazol-4-yl)benzamide, N-(5-cyano-1H-imidazol-4-yl)-3-chlorobenzamide, N-(5-cyano-1H-imidazol-4-yl)-3-fluorobenzamide, N-(5-cyano-1H-imidazol-4-yl)-4-fluorobenzamide, N-(5-cyano-1H-imidazol-4-yl)-3-methylbenzamide, N-(5-cyano-1H-imidazol-4-yl)phenylacetamide, 5-cyano-4-phenylmethylamino-1H-imidazole, N-(5-cyano-1H-imidazol-4-yl)-4-chlorobenzamide, N-(5-cyano-1H-imidazol-4-yl)-4-bromobenzamide, N-(5-cyano-1H-imidazol-4-yl)-4-pyridinecarboxamide, and N-(5-cyano-1H-imidazol-4-yl)-2-furancarboxamide.

19. The method of claim 15 wherein said substituted imidazole is N-(5-cyano-1H-imidazol-4-yl)benzamide.

20. The method of claim 15 wherein said locus is soybean plants.

21. The method of claim 20 wherein said substituted imidazole is applied at the $R_5$ or $R_6$ stage.

* * * * *